United States Patent
Reaves et al.

(10) Patent No.: US 9,662,444 B2
(45) Date of Patent: May 30, 2017

(54) EMPTY INFUSION SUPPLY CONTAINER ANNUNCIATOR AND DETECTION METHOD

(71) Applicant: CareFusion 303, Inc., San Diego, CA (US)

(72) Inventors: Adam Reaves, San Diego, CA (US); Lee Good, San Diego, CA (US); Pete Heffron, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 5 days.

(21) Appl. No.: 14/309,356

(22) Filed: Jun. 19, 2014

(65) Prior Publication Data

US 2015/0367070 A1    Dec. 24, 2015

(51) Int. Cl.
*A61M 31/00*    (2006.01)
*A61M 5/168*    (2006.01)

(52) U.S. Cl.
CPC ...... *A61M 5/16854* (2013.01); *A61M 5/1684* (2013.01); *A61M 2205/3348* (2013.01); *A61M 2205/3379* (2013.01); *A61M 2205/581* (2013.01); *A61M 2205/582* (2013.01); *A61M 2205/583* (2013.01)

(58) Field of Classification Search
CPC .............. A61M 5/168; A61M 5/16854; A61M 5/16831; A61M 5/1684; A61M 5/142; A61M 5/5086; A61M 2205/3348; A61M 2205/3379; A61M 2205/3386
USPC ................................ 604/506, 251, 253, 254
See application file for complete search history.

(56) References Cited

U.S. PATENT DOCUMENTS

| | | | |
|---|---|---|---|
| 3,034,504 A * | 5/1962 | Winsor | A61M 5/16886 251/9 |
| 3,942,526 A | 3/1976 | Wilder et al. | |
| 5,098,409 A * | 3/1992 | Stock | A61M 5/1684 128/DIG. 12 |
| 5,563,584 A * | 10/1996 | Rader et al. | 340/618 |
| 7,356,382 B2 | 4/2008 | Vanderveen | |
| 2011/0060758 A1 | 3/2011 | Schlotterbeck et al. | |
| 2011/0064612 A1* | 3/2011 | Franzoni et al. | 422/44 |
| 2011/0295191 A1* | 12/2011 | Injev | 604/22 |
| 2012/0209179 A1 | 8/2012 | Kamen et al. | |
| 2012/0234433 A1 | 9/2012 | Shih et al. | |
| 2014/0276426 A1 | 9/2014 | Borges et al. | |

FOREIGN PATENT DOCUMENTS

JP    10328301 A    12/1998

* cited by examiner

*Primary Examiner* — Edelmira Bosques
*Assistant Examiner* — Leah Swanson
(74) *Attorney, Agent, or Firm* — Fred C. Hernandez; Mintz Levin Cohn Ferris Glovsky and Popeo, P.C.

(57) ABSTRACT

A medical fluid infusion system includes a pump system configured to deliver a fluid drug to a patient. The system includes a device and method for detecting when the level of a fluid in a fluid supply container (such as an IV bag) is exhausted or near exhausted.

19 Claims, 3 Drawing Sheets

EMPTY INFUSION SUPPLY CONTAINER ANNUNCIATOR AND DETECTION METHOD

BACKGROUND

Intravenous (IV) fluid delivery pumps are used to deliver fluid to a patient or to draw out fluid from a patient's body. With constantly improving technologies and user needs, the demand for improved and integrated features has increased.

One such feature is the detection of an exhausted fluid supply container in the pump system. The fluid supply is often a fluid IV bag and the detection of empty fluid supply is sometimes referred to as "empty bag detection" although detection is not limited to bags as containers. In many instances supply containers provided to a clinician by hospital pharmacies or other soluble drug suppliers are over-filled or under-filled with respect to the stated volume of the supply container. The variations in supplied fluid volume may introduce an issue for infusion pumps that have been programmed to deliver a predetermined volume of fluid where the predetermined volume is the stated volume of fluid in the supply container.

In general, the infusion pump is not knowledgeable of how much fluid is in a bag beyond what a nurse or technician indicates to the pump. This inconsistency can results in two potential, problematic situations: premature exhaustion of available fluid can cause the introduction of air into the fluid delivery path or potentially expensive or critical drugs are wasted or not fully infused into the patient. These situations could signal secondary safety mechanisms because the empty bag was unsuccessfully detected. This introduces a need for the infusion pump to detect when a supply container is exhausted to prevent waste and to avoid a nurse or technician needlessly priming infusion sets filled with air.

SUMMARY

Described herein are medical fluid infusion systems including a pump system configured to deliver a fluid drug to a patient. The system includes a device and method for detecting when the level of a fluid in a fluid supply container (such as an IV bag) is exhausted or near exhausted.

In one aspect, there is disclosed a device to indicate a state of fluid in a fluid supply container of an infusion system, comprising: a fluid lumen having a first end and a second end, the first end fluidly coupled to a fluid container, wherein the fluid lumen has a variation in cross-sectional area that varies moving along the fluid lumen from the first end toward the second end, and wherein the variation in cross sectional area is defined by a predetermined profile; a pressure sensor in fluid communication with the fluid lumen so as to measure static fluid pressure in the fluid lumen, the static fluid pressure being based on a column height of fluid in the fluid lumen; and an indicator configured to generate a signal based upon a predetermined change in static fluid pressure as measured by the pressure sensor.

In another aspect, there is disclosed a method of detecting when a fluid container in a fluid pump system has a predetermined volume of fluid, the method comprising: providing an empty container detector that includes fluid lumen having a predetermined change in cross sectional area moving along a flow pathway of the fluid lumen, such that fluid flows through the empty container detector as it flows from the container to the end location; measuring a change in static fluid pressure as fluid flows through the lumen; and generating a signal that indicates a height of the fluid in the lumen is in a predetermined location in the lumen based on a predetermined static pressure change profile of fluid flowing through the lumen.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

Like reference symbols in the various drawings indicate like elements.

DETAILED DESCRIPTION

Described herein are medical fluid infusion systems including a pump system configured to deliver a fluid drug to a patient. The system includes a device and method for detecting when the level of a fluid in a fluid supply container (such as an IV bag) is exhausted or near exhausted.

Figure 1:
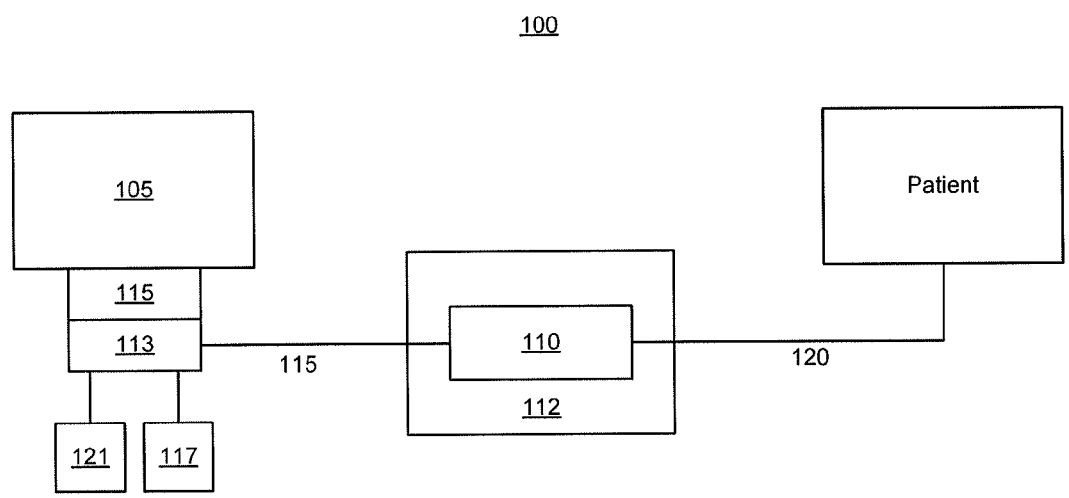
FIG. 1 is a schematic view of an infusion system according to one implementation.

FIG. 1 shows a schematic representation of a fluid infusion system 100. The fluid infusion system 100 is described herein in the context of being a bedside fluid drug infusion system for a patient although it should be appreciated that the features described herein may be used with any of a variety of fluid pumping systems and are not limited to drug infusion systems. In addition, the system described herein can be used for non-infusion devices.

With reference to FIG. 1, the infusion system 100 includes a fluid container, such as an intravenous (IV) bag 105, fluidly coupled to a patient via one or more fluid conduits, such as tubes 115 and 120. A pump device 112, such as a peristaltic pump, may drive fluid from the IV bag 105 toward the patient. The IV bag 105 contains a supply of fluid (such as a liquid drug or any other fluid) to be pumped to a patient. The pump device 112 is configured to pump fluid from the IV bag 105 toward a patient via a tube 120. In an embodiment, the pump device 112 includes a disposable IV set that removably couples with the pump device, such as the ALARIS® System from CareFusion Corporation (San Diego, Calif.). In another embodiment, the pump device 112 includes a removable pump cassette 110 that removably couples to the modular pump device 112 such as by inserting the pump cassette 110 into a seat of the modular pump device 112. The following U.S. patent application describes an exemplary pump system including a pump cassette and is incorporated by reference herein in its entirety: U.S. patent application Ser. No. 13/829,744 entitled "Modular Medical Device System", filed concurrently herewith.

The IV bag 105 is fluidly coupled to an empty container detector 115. The empty container detector 115 may be coupled to the fluid conduit at any of a variety of locations such as at the pump device 112. In an embodiment the empty container detector 115 is interposed between the IV bag 105 and an optional drip chamber 113 such that fluid from the IV bag 105 must flow through a fluid lumen of the empty container detector 115 before flowing into the drip chamber 113 and on toward the patient. When present, the drip chamber 113 may be used to prevent the introduction of air into the line upon empty bag detection.

A pressure sensor 121 is coupled to the empty container detector 115 so as to measure static fluid pressure in the fluid lumen. The empty container detector 115 can be positioned anywhere upstream of the pressure sensor 121. As described in detail below, the empty container detector 115 is configured to interact with the pressure sensor 121 to provide an indication to a user as to when fluid in the IV bag is at or near an empty state. In this regard, the system includes an indicator 117 configured to provide an indication to a user as to when the empty container detector 115 detects when the IV bag 105 is empty or near empty based on a signal generated by a signal generator coupled to the pressure sensor 121. The indicator 117 may provide any of an audio, visual, or tactile indication to the user. Moreover, the indicator 117 may be located anywhere or on any component of the system 100.

With reference still to FIG. 1, the tube 115 has a proximal end fluidly coupled to the IV bag 105, such as via the drip chamber. A distal end of the tube 115 is fluidly coupled to a fluid lumen of the pump cassette 110 (when used). Likewise, the tube 120 has a proximal end fluidly coupled to a fluid lumen of the pump cassette 110 and a distal end that attaches to the patient via an IV connection. Either of the tubes 115 or 120 may be formed of a single tube or may be formed of a series of tubes removably attached to one another, such as in an end-to-end manner using any of a variety of connectors such as Luer connectors. The tubes 115 and 120 and the fluid lumen of the pump cassette 110 collectively form a continuous fluid lumen that provides a fluid pathway from the IV bag 105 toward the patient. This continuous fluid lumen may include any of a variety of components that facilitate or otherwise are used in connecting the tubes and/or pumping fluid, including, for example, valves, filters, free-flow stop valves, pressure and air detection regions or components and access connectors, etc. Any of a variety of additional components may be used, including, for example, anti-free flow devices, pressure sensing components, air detection components, etc.

Empty Container Detector

Figure 2:
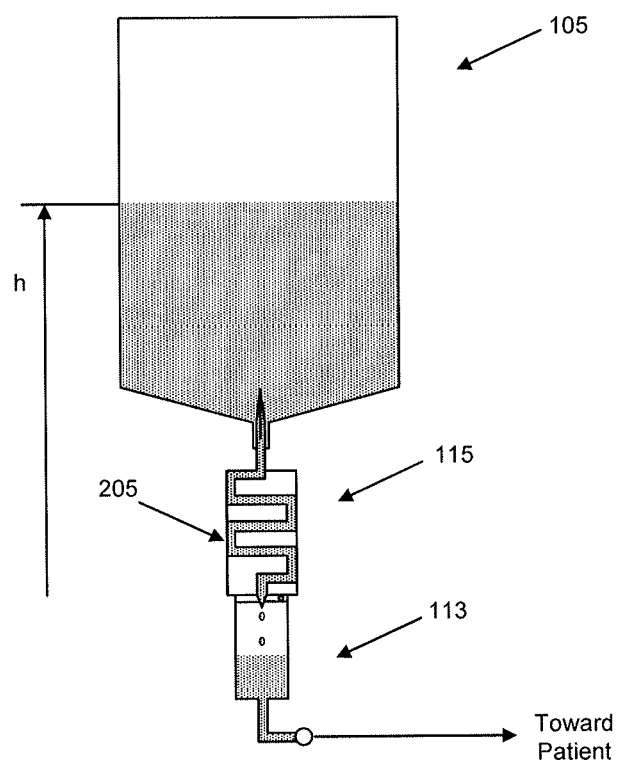
FIG. 2 shows an enlarged view of an IV bag, empty container detector, and drip chamber of the infusion system.

FIG. 2 shows an enlarged, schematic view of the IV bag 105, empty container detector 115, and drip chamber 113. It should be appreciated that FIG. 2 is not necessarily to scale. As mentioned, the empty container detector 115 is interposed between the IV bag 105 and the drip chamber 113 such that fluid F flows from the IV bag to the drip chamber 113 via a fluid lumen of the empty container detector 115. The fluid F has a fluid column height h measured relative to a reference. The height h decreases as fluid flows out of the bag due to pumping of the pump device 112. Thus, the height h is initially within the IV bag 105 and will gradually decrease to a location within the empty container detector 115 as fluid flows out of the IV bag 105.

The IV bag 105 may be any type of container for holding fluid and the drip chamber 113 may be any type of drip chamber. The empty container detector 115 may be a housing that defines a fluid lumen 205 for fluid to flow from the IV bag into the drip chamber 113. The fluid lumen 205 has a cross sectional area (along a direction normal to a vertical axis) that varies moving along the fluid lumen 205 from the IV bag 105 toward the drip chamber 113. In this regard, the variation in cross sectional area may be achieved for example by the fluid lumen 205 including at least one vertically oriented portion and at least one horizontally oriented portion. This achieves a back forth arrangement of vertical portions (of constant cross-sectional area) that step to horizontal portions (of different cross sectional area) at the junctions between the vertical portions and horizontal portions. It should be appreciated that the portions do not have to be completely vertical or horizontal but could also be inclined to include a vertical and horizontal component. In this case, the variation in cross sectional area would be gradual rather than stepped moving along the fluid lumen 205.

In the embodiment of FIG. 2, the fluid lumen 205 includes at least four vertical portions and three horizontal portions although the quantity of vertical and horizontal portions may vary. The cross sectional area of the fluid lumen 205 at a particular location along the fluid lumen 205 is based on whether the lumen 205 is formed by a vertical or horizontal portion. That is, the horizontal portions have larger cross sectional areas than cross sectional areas of the vertical portions.

The cross sectional area of the fluid lumen 205 has a direct effect on the rate of change of static fluid pressure as fluid flows out of the fluid lumen 205 into the drip chamber 113. As mentioned, the pressure sensor 121 measures static fluid pressure P, which is calculated per the following formula:

$$P = pgh$$

where P is static fluid pressure, p is fluid density, g is the gravitational constant, and h is the height of the fluid column. In the infusion system 100, fluid density is constant for the fluid drug. Gravitational constant is, by nature, a constant. Thus, the static fluid pressure is solely determined by the fluid column height h. Thus, the static fluid pressure will vary at a greater rate as the height h varies at a greater rate and will vary at a smaller rate as height h decreases at a smaller rate.

In an embodiment, the pump device 112 (FIG. 1) drives fluid F out of the IV bag 105 at a constant rate. Thus, a constant volume of fluid is displaced per unit time from the IV bag and through the lumen 205 of the empty container detector 115. Due to the variation on cross sectional area moving along the vertical portions and horizontal portions of the lumen 205, the static pressure (as measured by the pressure sensor 121) varies in a predictable manner between a high-pressure change rate and low-pressure change rate based on whether the column height H is in a location of greater or smaller cross sectional area. In other words, the static pressure curve changes from a fast rate of change (in the vertical portions with a smaller cross sectional area) to a slow rate of change (in the horizontal portions with a greater cross sectional area) and so on. When the modification in cross sectional area is repeated one or more times, the static pressure signature is identifiable by the pressure sensor 121.

Figure 3:
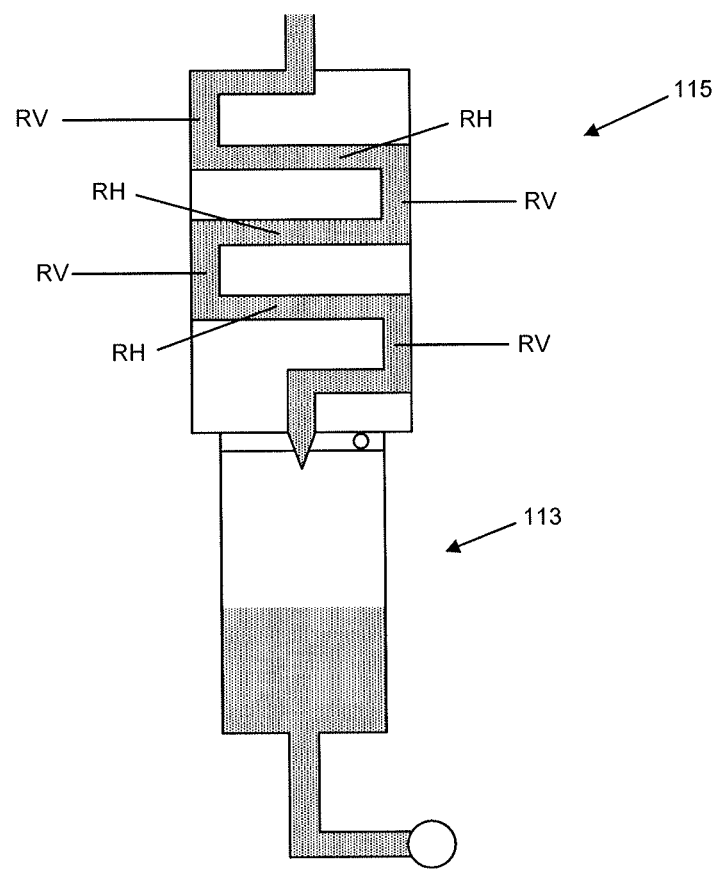
FIG. 3 shows an enlarged view of the empty container detector and drip chamber of the infusion system.

This concept is graphically represented in FIG. 3, which shows an enlarged view of the empty container detector 115. Assuming fluid flows out of the fluid lumen 205 of the empty container detector 115 at a constant flow rate, the fluid column height h decreases at a greater rate RV through the vertical portions than the rate of change RH through the horizontal portions due to the greater cross sectional area of the horizontal portions relative to the vertical portions. In other words, the static pressure (which is a function of the fluid column height h) undergoes a greater rate of change through the vertical portions relative to the horizontal portions.

The particular geometry of the fluid lumen 205 (and the changes in geometry of the fluid lumen moving from the IV bag toward the drip chamber) can be used to form a predictable and repeatable pressure change profile for fluid flowing through the fluid lumen 205, and is not limited to those represented here. With prior knowledge of the pressure change profile, a user can determine the location of the column height h and whether the column height h is near the end of the fluid lumen 205 or approaching the end of the fluid lumen, which is an indication that the IV bag is empty or near empty.

The pressure sensor may have access to software that has been programmed to map the pressure change profile (based on the predetermined geometry of the lumen 205). Based on recognition of the pressure change profile that corresponds to particular locations of the lumen 205, the pressure sensor may send a signal to the indicator 117 to notify the user that the fluid column height is near the end of the lumen and that the bag is empty.

Pursuant to a corresponding method, there is provided an empty container detector that includes fluid lumen having a predetermined and recognizable change in cross sectional area moving along a flow pathway of the fluid lumen. The empty container detector is positioned along a fluid pathway that spans from a container of fluid (such as an IV bag) to an end location (such as an access site for a patient) such that fluid flows through the empty container detector as it flows from the container to the end location. A pressure sensor is also provided to measure static fluid pressure within the lumen. In an embodiment, the fluid lumen includes one or more horizontal portions and one or more vertical portions that vary the cross sectional area of the fluid lumen.

Based on knowledge of the variation in cross sectional area moving through the fluid lumen, a static pressure change profile is created, wherein the profile represents a location of the column height of fluid in the fluid lumen. The pressure sensor generates an encoded signal that represents the location of the column height of the fluid. When the column height of fluid reaches a predetermined location in the fluid lumen of the empty container detector 115, a signal is sent to notify the user. The predetermined location of the column height may correspond to a location that indicates the IV bag is nearing an empty state or at an empty state.

The infusion systems described herein can be used with existing infusion pumps such as the ALARIS System (CareFusion, San Diego, Calif.) or infusion pumps described in U.S. Pat. No. 7,356,382, which is incorporated by reference herein. It should also be appreciated that the described infusion systems are not limited to intravenous infusions, but can be used for any number of infusion types to a patient through a catheter including but not limited to parenteral, intraarterial, intracardiac, intraosseous, intramuscular, intrathecal, intraperitoneal, epidural, intracerebral, gastrointestinal, and the like. In addition, the infusion systems described herein can be used in conjunction with any of a variety of electronic and/or software medication management systems, such as the system described in U.S. Patent Publication 2011/0060758 to Schlotterbeck. U.S. Patent Publication 2011/0060758 is incorporated herein by reference in its entirety.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) when depicted in the accompanying figures and/or described herein do not necessarily require the particular order shown, or sequential order, to achieve desirable results. Other implementations may be within the scope of the following claims.

What is claimed is:

1. A device to indicate a state of fluid in a fluid supply container of an infusion system, comprising:
   a fluid lumen having a first end and a second end, the first end fluidly coupled to a fluid container, wherein the fluid lumen defines a flow pathway with a first point along the pathway having a first cross-sectional area that varies relative to a second cross-sectional area at a second point along the pathway moving along the fluid lumen from the first end toward the second end, and wherein the cross-sectional area of any point along the pathway remains constant relative to itself, and wherein the cross sectional area moving along the pathway varies as defined by a predetermined, fixed profile, wherein the second end of the fluid lumen is connected to a drip chamber of a drug infusion system such that fluid flows from the fluid lumen into the drip chamber;
   wherein the fluid lumen includes a series of elongated, horizontally oriented portions through which fluid flows in a horizontal direction and a series of elongated, vertically oriented portions through which fluid flows in a distal direction, and wherein the horizontally oriented portions and vertically oriented portions are connected by a series of bends in the fluid lumen;
   a pressure sensor in fluid communication with the fluid lumen so as to measure static fluid pressure in the fluid lumen, the static fluid pressure being based on a column height of fluid in the fluid lumen; and
   an indicator configured to generate a signal based upon a predetermined change in static fluid pressure as measured by the pressure sensor.

2. The device as in claim 1, wherein the indicator generates a signal when the change in static fluid pressure corresponds to the fluid column height being at a location near the second end of the fluid lumen.

3. The device as in claim 1, wherein the indicator generates a signal subsequent to a change in static fluid pressure wherein the change in static fluid pressure corresponds to a predetermined fluid column height, pressure, or fluid flow characteristic of the fluid lumen.

4. The device as in claim 3, wherein the second end of the fluid lumen is a vertically oriented portion of the fluid lumen.

5. The device as in claim 3, wherein static fluid pressure undergoes a predetermined rate of change when a terminus of the fluid column traverses a predetermined section of the fluid lumen.

6. The device as in claim 1, wherein the first end of the fluid lumen is connected to an intravenous (IV) bag of a drug infusion system.

7. The device as in claim 1, wherein the signal is an audio signal.

8. The device as in claim 1, wherein the signal is a visual signal.

9. The device as in claim 1, wherein the signal is a tactile signal.

10. The device as in claim 1, wherein the signal is an electronic signal.

11. The device as in claim 1, wherein the signal is an electronic signal sent to at least one of a care provider, a portable electronic device, and a hospital information system.

12. The device as in claim 1, wherein the infusion system is an infusion pump system.

13. The device as in claim 1, wherein the fluid lumen zig zags between the elongated, horizontally oriented portions and the vertically oriented portions.

14. A method of detecting when a fluid container in a fluid pump system has a predetermined volume of fluid, the method comprising:

providing an empty container detector that includes a fluid lumen that defines a flow pathway with a first point along the pathway having first cross-sectional area that varies relative to a second cross-sectional area at a second point along the pathway moving along the fluid lumen from a first end toward a second end, and wherein the cross-sectional area of any point along the pathway remains constant relative to itself, such that fluid flows through the empty container detector as it flows from the container to an end location of the fluid lumen and into a drip chamber and wherein the fluid lumen includes a series of elongated, horizontally oriented portions through which fluid flows in a horizontal direction and a series of elongated, vertically oriented portion through which fluid flows in a distal direction, and wherein the horizontally oriented portions and vertically oriented portions are connected by a series of bends in the fluid lumen;

measuring a change in static fluid pressure as fluid flows through the lumen; and generating a signal that indicates a height of the fluid in the lumen is in a predetermined location in the lumen based on a predetermined static pressure change profile of fluid flowing through the lumen.

15. The method as in claim 14, wherein the empty container detector is positioned along a fluid pathway that spans from a container of fluid to an end location.

16. The method as in claim 14, wherein the container of fluid is an IV bag.

17. The method as in claim 14, wherein the end location is a patient access site.

18. The method as in claim 14, wherein the fluid pump system is a drug infusion system.

19. The method as in claim 14, wherein the fluid lumen wherein the fluid lumen zig zags between the elongated, horizontally oriented portions and the vertically oriented portions.

* * * * *